United States Patent
Okamoto et al.

(10) Patent No.: US 9,137,985 B2
(45) Date of Patent: Sep. 22, 2015

(54) ARTHROPOD PEST CONTROL COMPOSITION

(71) Applicant: SUMITOMO CHEMICAL COMPANY, LIMITED, Tokyo (JP)

(72) Inventors: Hiroshi Okamoto, Takarazuka (JP); Kenji Yoshimura, Kuki (JP); Takashi Tanaka, Kuki (JP); Masato Mizutani, Osaka (JP); Shinobu Kawaguchi, Osaka (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 65 days.

(21) Appl. No.: 14/157,980

(22) Filed: Jan. 17, 2014

(65) Prior Publication Data

US 2014/0205547 A1    Jul. 24, 2014

(30) Foreign Application Priority Data

Jan. 23, 2013  (JP) ................. 2013-010414

(51) Int. Cl.
| | |
|---|---|
| *A61K 9/12* | (2006.01) |
| *A01N 25/00* | (2006.01) |
| *A01N 37/18* | (2006.01) |
| *C07D 277/00* | (2006.01) |
| *A01N 25/06* | (2006.01) |
| *A01N 25/02* | (2006.01) |
| *A01N 59/04* | (2006.01) |

(52) U.S. Cl.
CPC ................ *A01N 25/06* (2013.01); *A01N 25/02* (2013.01); *A01N 59/04* (2013.01)

(58) Field of Classification Search
None
See application file for complete search history.

(56) References Cited

U.S. PATENT DOCUMENTS

| | | | |
|---|---|---|---|
| 5,034,404 A | 7/1991 | Uneme et al. | |
| 5,489,603 A | 2/1996 | Uneme et al. | |
| 5,633,375 A | 5/1997 | Uneme et al. | |
| 6,253,340 B1 * | 6/2001 | Cowles et al. ................. | 714/718 |
| 2007/0134595 A1 * | 6/2007 | Miller ............................ | 430/300 |
| 2008/0319023 A1 | 12/2008 | Richman et al. | |
| 2010/0016384 A1 | 1/2010 | Sembo | |
| 2010/0144888 A1 * | 6/2010 | Bessette ........................ | 514/690 |

FOREIGN PATENT DOCUMENTS

| | | | | |
|---|---|---|---|---|
| JP | 2006-169170 A | | 6/2006 | |
| JP | 2008-201710 A | | 9/2008 | |
| JP | 2009-275021 A | | 11/2009 | |
| WO | WO 2010/129345 | * | 11/2010 | ............. A01N 47/02 |
| WO | WO 2011/025789 | * | 3/2011 | ............. A01N 25/16 |
| WO | WO 2012/057260 | * | 5/2012 | ............. A01N 43/52 |

OTHER PUBLICATIONS

SciFinder search results; downloaded May 14, 2015; 2 pages.*

* cited by examiner

*Primary Examiner* — Jeffrey T Palenik
(74) *Attorney, Agent, or Firm* — Birch, Stewart, Kolasch & Birch, LLP

(57) ABSTRACT

Provided is an arthropod pest control composition, the composition having an superior effect on control of arthropod pests. The composition comprises 0.01 to 0.5% by weight of a neonicotinoid insecticidal compound, 10 to 50% by weight of an organic solvent selected from the group consisting of monoalcohols having 1 to 3 carbon atoms and acetone, and 49.5 to 89.99% by weight of liquefied carbon dioxide, wherein the weight of ethanol to that of the neonicotinoid insecticidal compound is 100 times or more.

16 Claims, No Drawings

ARTHROPOD PEST CONTROL COMPOSITION

BACKGROUND OF THE INVENTION

1. Field of the Invention

The present invention relates to an arthropod pest control composition and a method for controlling arthropod pests.

2. Background Art

It has been known that neonicotinoid insecticidal compounds such as clothianidin have an excellent effect on control of arthropod pests (see, for example, JP-A-3-157308, JP-A-2008-201710, and JP-A-2008-201731). However, a part of arthropod pests inhabiting indoors lies concealed in clearances between furnishings such as sofas and furniture, the undersides of coverings such as carpets, and clearances between beddings such as mattresses and futons. There is the case where the neonicotinoid insecticidal compounds which are solids at normal temperature cannot exhibit a sufficient effect when it is applying to an indoor agent for controlling arthropod pests. Therefore it has been desired to develop a control composition appropriate to control such arthropod pests.

SUMMARY OF INVENTION

It is an object of the present invention to provide a arthropod pest control composition, the composition containing, as an active component, a neonicotinoid insecticidal compound such as clothianidin, nitenpyram, imidacloprid, acetamiprid, thiamethoxam, and thiacloprid, and having an excellent effect.

The present inventors have made earnest studies and, as a result, found that a composition comprising a neonicotinoid insecticidal compound, an organic solvent selected from the group consisting of monoalcohols having 1 to 3 carbon atoms and acetone, and liquefied carbon dioxide in a specific proportion, is useful as a composition for controlling arthropod pests among compositions containing, as its active component, a neonicotinoid insecticidal compound such as clothianidin, imidacloprid, thiamethoxam, thiacloprid, nitenpyram, and acetamiprid, and have led to the completion of the present invention.

That is, the present invention is as follows.

[1] An arthropod pest control composition, the composition comprising 0.01 to 0.5% by weight of a neonicotinoid insecticidal compound, 10 to 50% by weight of an organic solvent selected from the group consisting of monoalcohols having 1 to 3 carbon atoms and acetone, and 49.5 to 89.99% by weight of liquefied carbon dioxide, wherein the weight of the organic solvent to that of the neonicotinoid insecticidal compound is 100 times or more.

[2] The arthropod pest control composition according to [1], wherein the neonicotinoid insecticidal compound is clothianidin.

[3] The arthropod pest control composition according to [1] or [2], wherein the organic solvent is ethanol or acetone.

[4] The arthropod pest control composition according to any one of [1] to [3], wherein the content of the neonicotinoid insecticidal compound is 0.01 to 0.2% by weight.

[5] An agent for controlling arthropod pests, the agent being obtained by filling the composition for controlling arthropod pests according to anyone of [1] to [4] in a pressure container.

[6] A method for controlling arthropod pests, the method including spraying the arthropod pest control composition according to any one of [1] to [4] on a place where arthropod pests inhabit, from the pressure container.

[7] The control method according to [6], wherein the place where arthropod pests inhabit is an indoor space.

Arthropod pests can be controlled by the present invention.

DETAILED DESCRIPTION OF THE PREFERRED EMBODIMENTS

The composition for controlling arthropod pests of the present invention is an arthropod pest control composition, the composition comprising 0.01 to 0.5% by weight of a neonicotinoid insecticidal compound, 10 to 50% by weight of an organic solvent selected from the group consisting of monoalcohols having 1 to 3 carbon atoms and acetone (hereinafter referred to as "present organic solvent"), and 49.5 to 89.99% by weight of liquefied carbon dioxide, wherein the weight of the present organic solvent to that of the neonicotinoid insecticidal compound is 100 times or more. Hereinafter, the said composition is referred to as "present invention composition". The present invention composition is filled in a pressure container because liquefied carbon dioxide easily vaporizes under atmospheric pressure.

Examples of the neonicotinoid insecticidal compound in the present invention include clothianidin, imidacloprid, thiamethoxam, thiacloprid, nitenpyram, and acetamiprid, and preferable examples thereof include clothianidin, imidacloprid, thiamethoxam, and thiacloprid.

In the present invention, the neonicotinoid insecticidal compound may be either one or a mixture of two or more of the compounds recited above.

Any monoalcohol having 1 to 3 carbon atoms in the present organic solvent in the present invention is a monoalcohol selected from the group consisting of methanol, ethanol, propanol, and isopropanol.

The present organic solvent may be either one or a mixture of two or more selected from the group consisting of methanol, ethanol, propanol, and isopropanol.

As the container in which the present invention composition is filled, a 1 to 50 L pressure container made of a material such as iron, aluminum, or stainless is usually used. The pressure container is usually equipped with a pressure valve at an opening portion of the main body of the pressure container, and a nozzle or the like that is used to spray the present invention composition may attach to the pressure valve, if necessary.

Usually, about 5 to 7 kg of the present invention composition is filled in the pressure container having a volume of about 10 L.

The pressure in the pressure container is usually about 5 MPa to 40 MPa at room temperature.

All of clothianidin, nitenpyram, imidacloprid, acetamiprid, thiamethoxam, and thiacloprid described above are known insecticidal compounds, and are described, for example, in The Pesticide Manual-15th edition (Published from BCPC); ISBN 978-1-901396-18-8" pp. 229, 817, 645, 9, 1112, and 1111. These compounds may be extracted from commercially available preparations or may be produced by a known method.

As ethanol, methanol, propanol, isopropanol, and acetone which may be contained in the present invention composition, any of standard products for industries, drugs, or cosmetics can be used. When the amount of the present organic solvent is less than 100 times that of the neonicotinoid insecticidal compound, there is the case where the neonicotinoid insecticidal compound cannot exhibit a sufficient effect on control of harmful organisms inhabiting in clearances between furnishings and the undersides of coverings when the present invention composition is applied. Although the amount of the present organic solvent may be 100 times or more that of the neonicotinoid insecticidal compound, the amount of the present organic solvent in the present invention composition is 10 to 50% by weight in practice because there is the case where walls or floors are wet with the present organic solvent when the present invention composition is applied indoors.

Also as liquefied carbon dioxide contained in the present invention composition, any of standard products for industries or foods may be used.

When the present invention composition is prepared, usually, the neonicotinoid insecticidal compound and the present organic solvent are poured into the pressure container and then liquefied carbon dioxide is poured into the pressure container under pressure condition to prepare the present invention composition.

When the present invention composition is used to control arthropod pests, the present invention composition may be sprayed directly to the arthropod pests. In this case, the amount to be sprayed and the like are controlled so that the composition can reach the place where arthropod pests inhabit.

In the case where the arthropod pests inhabit indoors, the composition is sprayed so that clothianidin that is an active component can reach clearances between furnishings such as sofas and furniture, the undersides of coverings such as carpets, and clearances between beddings such as mattresses and futons. In this case, when the present invention composition is sprayed in a large amount, it is necessary to carry out the spray operation with great care so that vaporized carbon dioxide can not cause oxygen deficiency.

As arthropod pests on which the present invention composition has an effect, the following examples are given.

Lepidoptera pests: Pyralidae such as *Plodia interpunctella*, Tineidae such as *Tinea translucens* and *Tineola bisselliella*, and the like;

Diptera pests: *Culex* such as *Culex pipiens pallens*, *Culex tritaeniorhynchus*, and *Culex quinquefasciatus*, *Aedes* spp. such as *Aedes aegypti* and *Aedes albopictus*, *Anopheles* spp. such as *Anopheles sinensis*, Chironomidae, Muscidae such as *Musca domestica* and *Muscina stabulans*, Calliphoridae, Sarcophagidae, Fanniidae, Anthomyiidae such as *Delia platura* and *Delia antique*, Drosophilidae, Phoridae such as *Megaselia spiracularis*, Psychodidae such as *Clogmia albipunctata*, Sciaridae, Simuliidae, Ceratopogonidae, and the like;

Dictyoptera pests: *Blattella germanica*, *Periplaneta fuliginosa*, *Periplaneta americana*, *Periplaneta brunnea*, *Blatta orientalis*, and the like;

Hymenoptera pests: Formicidae such as *Monomorium pharaosis*, *Formica fusca japonica*, *Ochetellus glaber*, *Pristomyrmex pungens*, *Pheidole noda*, *Acromyrmex* spp. *Solenopsis* spp., *Linepithema humile*, Vespidae, Bethylidae, and the like;

Siphonaptera pests: *Ctenocephalides felis*, *Ctenocephalides canis*, *Pulex irritans*, *Xenopsylla cheopis*, and the like;

Anoplura pests: *Pediculus humanus corporis*, *Pediculus humanus humanus*, *Phthirus pubis*, *Haematopinus eurysternus*, *Dalmalinia ovis*, *Haematopinus suis*, *Linognathus setosus*, and the like;

Isoptera pests: *Reticulitermes speratus*, *Coptotermes formosanus*, and the like;

Hemiptera pests: Delphacidae such as *Laodelphax striatellus*, *Nilaparvata lugens*, and *Sogatella furcifera*, Deltocephalidae such as *nephotettix cincticeps*, and *Nephotettix virescens*, Cimicidae such as *Cimex lectularius* and *Cimex hemipterus*, Psyllidae, and the like;

Coleoptera pests: Dermestidae such as *Anthrenus verbasci* and *Dermestes maculates*, Anobiidae such as *lasioderma serricorne*, Scolytidae such as *Lyctus brunneus* and *Tomicus piniperda*, Bostrichidae, Ptinidae, and the like; and Acarina: Acaridae such as *Tyrophagus putrescentiae*, Dermanyssidae such as *Dermatophagoides farinae* and *Dermatophagoides ptrenyssnus*, Cheyletidae such as *Cheyletus eruditus*, *Cheyletus malaccensis*, *Cheyletus moorei*, and *Cheyletiella yasguri*, Leptotrombidium such as *Leptotrombidium akamushi*, Ixodidae such as *Haemaphysalis longicornis*, and the like.

The present invention composition has an excellent effect on control of hardly controllable arthropod pests such as *Cimex lectularius* and *Cimex hemipterus* which inhabit indoors and lie concealed in clearances.

The present invention composition may contain an insecticidal compound other than the neonicotinoid insecticidal compound. Examples of the insecticidal compound include pyrethroid compounds such as allethrin, tetramethrin, prallethrin, phenothrin, resmethrin, cyphenothrin, permethrin, cypermethrin, α-cypermethrin, ζ-cypermethrin, deltamethrin, tralomethrin, cyfluthrin, β-cyfluthrin, cyhalothrin, λ-cyhalothrin, Furamethrin, imiprothrin, ethofenprox, fenvalerate, esfenvalerate, fenpropathrin, silafluofen, bifenthrin, transfluthrin, flucythrinate, τ-fluvalinate, acrinathrin, tefluthrin, cycloprothrin, and empenthrin, and organic phosphorous compounds such as dichlorvos, fenitrothion, cyanophos, profenophos, sulprofos, phenthoate, isoxathion, tetrachlorovinphos, fenthion, chlorpyrifos, diazinon, acephate, terbufos, phorate, chloroethoxyfos, fosthiazate, ethoprophos, cadusafos, and methidathion.

EXAMPLES

The present invention will be specifically described by way of Examples such as Preparation Examples and Test Examples.

First, Preparation Examples of the present invention composition and an agent for controlling arthropod pests being obtained by filling the present invention composition are described.

Preparation Example 1

Into a pressure container were charged 0.1 parts by weight of clothianidin and 20 parts by weight of ethanol in advance, a pressure valve was attached to the pressure container, and then 79.9 parts by weight of liquefied carbon dioxide was poured from the nozzle side to prepare present invention composition 1.

Preparation Example 2

Into a pressure container were charged 0.05 parts by weight of clothianidin and 20 parts by weight of acetone in advance, a pressure valve was attached to the pressure container, and then 79.95 parts by weight of liquefied carbon dioxide was poured from the nozzle side to prepare present invention composition 2.

Preparation Example 3

Into a pressure container were charged 0.2 parts by weight of clothianidin and 20 parts by weight of ethanol in advance, a pressure valve was attached to the pressure container, and then 79.8 parts by weight of liquefied carbon dioxide was poured from the nozzle side to prepare present invention composition 3.

Preparation Example 4

Into a pressure container were charged 0.05 parts by weight of imidacloprid and 10 parts by weight of ethanol in advance, a pressure valve was attached to the pressure container, and then 89.95 parts by weight of liquefied carbon dioxide was poured from the nozzle side to prepare present invention composition 4.

Preparation Example 5

Into a pressure container were charged 0.05 parts by weight of thiamethoxam and 10 parts by weight of ethanol in advance, a pressure valve was attached to the pressure container, and then 89.95 parts by weight of liquefied carbon dioxide was poured from the nozzle side to prepare present invention composition 5.

Preparation Example 6

Into a pressure container were charged 0.05 parts by weight of thiacloprid and 10 parts by weight of ethanol in advance, a pressure valve was attached to the pressure container, and then 89.95 parts by weight of liquefied carbon dioxide was poured from the nozzle side to prepare present invention composition 6.

Preparation Example 7

Into a pressure container were charged 0.05 parts by weight of nitenpyram and 10 parts by weight of ethanol in advance, a pressure valve was attached to the pressure container, and then 89.95 parts by weight of liquefied carbon dioxide was poured from the nozzle side to prepare present invention composition 7.

Preparation Example 8

Into a pressure container were charged 0.05 parts by weight of acetamiprid and 10 parts by weight of ethanol in advance, a pressure valve was attached to the pressure container, and then 89.95 parts by weight of liquefied carbon dioxide was poured from the nozzle side to prepare present invention composition 8.

Preparation Example 9

Into a pressure container are charged 0.05 parts by weight of clothianidin and 10 parts by weight of methanol in advance, a pressure valve is attached to the pressure container, and then 89.95 parts by weight of liquefied carbon dioxide is poured from the nozzle side to prepare present invention composition 9.

Preparation Example 10

Into a pressure container are charged 0.05 parts by weight of clothianidin and 10 parts by weight of propanol in advance, a pressure valve is attached to the pressure container, and then 89.95 parts by weight of liquefied carbon dioxide is poured from the nozzle side to prepare present invention composition 10.

Preparation Example 11

Into a pressure container was charged 0.05 parts by weight of clothianidin and 10 parts by weight of isopropanol in advance, a pressure valve is attached to the pressure container, and then 89.95 parts by weight of liquefied carbon dioxide is poured from the nozzle side to prepare present invention composition 11.

Preparation Example 12

Into a pressure container were charged 0.1 parts by weight of clothianidin and 15 parts by weight of ethanol in advance, a pressure valve was attached to the pressure container, and then 84.9 parts by weight of liquefied carbon dioxide was poured from the nozzle side to prepare present invention composition 12.

Preparation Example 13

Into a pressure container were charged 0.1 parts by weight of clothianidin and 30 parts by weight of ethanol in advance, a pressure valve was attached to the pressure container, and then 69.9 parts by weight of liquefied carbon dioxide was poured from the nozzle side to prepare present invention composition 13.

Preparation Example 14

Into a pressure container were charged 0.1 parts by weight of clothianidin and 40 parts by weight of ethanol in advance, a pressure valve was attached to the pressure container, and then 59.9 parts by weight of liquefied carbon dioxide was poured from the nozzle side to prepare present invention composition 14.

The following comparative control agents were prepared for comparison with the present invention composition. Comparative Preparation Example 1

Into an aerosol can were charged 0.2 parts by weight of clothianidin and 49.8 parts by weight of an aliphatic saturated hydrocarbon solvent (neothiozole; manufactured by Chuo Kasei Co., Ltd.). After an aerosol valve was attached to the aerosol can, 25 parts by weight of dimethyl ether and 25 parts by weight of liquefied natural gas were filled in the aerosol can and then it was shaken. Moreover, a whole amount releasing type aerosol actuator was attached to the aerosol can to prepare comparative composition 1.

Comparative Preparation Example 2

Into a pressure container were charged 0.1 parts by weight of clothianidin and 5 parts by weight of ethanol in advance, a pressure valve was attached to the pressure container, and then 94.9 parts by weight of liquefied carbon dioxide was poured from the nozzle side to prepare comparative composition 2.

Next, the following Test Examples show that the present invention composition has an excellent effect on control of arthropod pests.

Test Example 1

Two rods having a thickness of 2 mm and length of 3 cm were sandwiched between two square (3 cm×3 cm) plywood boards, while being placed on two sides of the boards, so as to form a space, and 10 adult bed bugs were then allowed to lie concealed in the space. This workpiece was placed in a plastic cup (lidless), and then it was disposed on the floor of a closed room (4 m×3 m×2.3 m (height)). The present invention composition prepared in Preparation Example 1 was sprayed in an amount of 10 g/m³ (total spray amount=280 g). The plastic cup was recovered 18 hours after the composition was sprayed, and kept in the condition of room temperature for 24 hours to determine the mortality of the adult bed bugs.

As a comparative control, the comparative composition prepared in Comparative Preparation Example 1 was sprayed in an amount of 5 g/m³ (140 g, 0.28 g as clothianidin). The mortality was determined in the same manner. The results were shown in Table 1.

TABLE 1

|  | Mortality (%) |
|---|---|
| Present invention composition 1 | 93.3 |
| Comparative composition 1 | 6.7 |

Test Example 2

Adult bed bugs in were put on the floor of the room used in Test Example 1, and 10 g/m³ (total spray amount=280 g) of present invention composition 1 was sprayed. The cups in which the bed bugs were put was recovered 16 hours after the spraying, and kept in the condition of room temperature to determine the mortality of the bed bugs after 14 days. Present invention compositions 12 to 14 prepared in Preparation Examples 12 to 14 were sprayed to determine the mortality of the bed bugs after 14 days in the same manner, respectively.

As a comparative control, the comparative composition prepared in Comparative Preparation Example 2 was sprayed in an amount of 10 g/m³ (total spray amount=280 g) and the mortality was determined after 14 days in the same manner.

TABLE 2

|  | Mortality (%) |
|---|---|
| Present invention composition 1 | 100 |
| Present invention composition 12 | 100 |
| Present invention composition 13 | 100 |
| Present invention composition 14 | 95 |
| Comparative composition 2 | 10 |

The present invention composition exhibits an excellent effect on control of arthropod pests and can exterminate bed bugs which are hardly controllable arthropod pests.

What is claimed is:

1. An arthropod pest control composition, the composition comprising 0.01 to 0.5% by weight of a neonicotinoid insecticidal compound, 10 to 50% by weight of an organic solvent selected from the group consisting of monoalcohols having 1 to 3 carbon atoms and acetone, and 49.5 to 89.99% by weight of liquefied carbon dioxide, wherein the weight of the organic solvent to that of the neonicotinoid insecticidal compound is 100 times or more.

2. The arthropod pest control composition according to claim 1, wherein the neonicotinoid insecticidal compound is clothianidin.

3. The arthropod pest control composition according to claim 1, wherein the organic solvent is ethanol or acetone.

4. The arthropod pest control composition according to claim 1, wherein the content of the neonicotinoid insecticidal compound is 0.01 to 0.2% by weight.

5. An agent for controlling arthropod pests, the agent being obtained by filling the composition for controlling arthropod pests according to claim 1 in a pressure container.

6. A method for controlling arthropod pests, the method comprising spraying the arthropod pest control composition according to claim 1 on a place where arthropod pests inhabit, from the pressure container.

7. The control method according to claim 6, wherein the place where arthropod pests inhabit is an indoor space.

8. An agent for controlling arthropod pests, the agent being obtained by filling the composition for controlling arthropod pests according to claim 2 in a pressure container.

9. An agent for controlling arthropod pests, the agent being obtained by filling the composition for controlling arthropod pests according to claim 3 in a pressure container.

10. An agent for controlling arthropod pests, the agent being obtained by filling the composition for controlling arthropod pests according to claim 4 in a pressure container.

11. A method for controlling arthropod pests, the method comprising spraying the arthropod pest control composition according to claim 2 on a place where arthropod pests inhabit, from the pressure container.

12. A method for controlling arthropod pests, the method comprising spraying the arthropod pest control composition according to claim 3 on a place where arthropod pests inhabit, from the pressure container.

13. A method for controlling arthropod pests, the method comprising spraying the arthropod pest control composition according to claim 4 on a place where arthropod pests inhabit, from the pressure container.

14. The control method according to claim 11, wherein the place where arthropod pests inhabit is an indoor space.

15. The control method according to claim 12, wherein the place where arthropod pests inhabit is an indoor space.

16. The control method according to claim 13, wherein the place where arthropod pests inhabit is an indoor space.

* * * * *